United States Patent [19]

Mondani et al.

[11] Patent Number: 5,087,201
[45] Date of Patent: Feb. 11, 1992

[54] SELF-THREADING PIN FOR THE IMPLANTATION OF DENTAL PROSTHESIS

[76] Inventors: Luigi P. Mondani, 1723 Corso Europa, Genova-Quinto; Maria P. Mondani, 12, via S. Bartolomeo, Camogli, both of Italy

[21] Appl. No.: 571,831

[22] Filed: Aug. 22, 1990

Related U.S. Application Data

[63] Continuation of Ser. No. 277,264, Nov. 29, 1988, abandoned.

[30] Foreign Application Priority Data

Dec. 4, 1987 [IT] Italy ............... 12594 A/87

[51] Int. Cl.$^5$ ............................................. A61C 8/00
[52] U.S. Cl. ................................ 433/174; 433/225
[58] Field of Search ................ 433/225, 221, 174

[56] References Cited

U.S. PATENT DOCUMENTS

| 3,861,043 | 1/1975 | Lieb et al. | 433/225 |
| 4,171,569 | 10/1979 | Rovins | 433/225 |
| 4,187,611 | 2/1980 | Chan | 433/225 |
| 4,365,958 | 12/1982 | Vlock | 433/225 |
| 4,746,294 | 5/1988 | Colombo et al. | 433/174 |

FOREIGN PATENT DOCUMENTS

| 0237505 | 9/1987 | European Pat. Off. | |
| 2812175 | 9/1979 | Fed. Rep. of Germany | 433/221 |
| 0701030 | 4/1987 | Fed. Rep. of Germany | |
| 1420594 | 11/1965 | France | |
| 2050198 | 4/1971 | France | |
| 2395738 | 1/1979 | France | |

*Primary Examiner*—Gene Mancene
*Assistant Examiner*—Adriene B. Lepiane
*Attorney, Agent, or Firm*—Larson and Taylor

[57] ABSTRACT

A self-threading pin (1) for the implantation of a dental prosthesis is formed at one end with a drill bit (2). The screw threaded portion (3) of the pin (1) is provided with longitudinal flutes (5) for discharging the drilled material, departing from the rear end of the discharge grooves (4) of the drill bit (2) and extending along the whole length of the screw threaded portion (3) of the pin (1). The head (6) of the pin has a polygonal cross sectional shape for driving the pin by a tool.

8 Claims, 1 Drawing Sheet

SELF-THREADING PIN FOR THE IMPLANTATION OF DENTAL PROSTHESIS

This application is a continuation of application Ser. No. 07/277,264 filed Nov. 29, 1988 and abandoned Aug. 22, 1990.

BACKGROUND AND SUMMARY OF THE INVENTION

This invention relates to anchoring pins of the type which are screw threaded into the maxilla bone of a patient, for the implantation of a dental prosthesis.

At present, self-threading conical shaped pins are used, which are screw threaded into the maxilla bone. For this purpose it is necessary to make a bore of a suitable size into the maxilla bone. If this bore is too small, during the screwing of the self-threading pin tensions may be created tending to deform the maxilla bone. If this bore is too large, the fastening of the pin is unstable. In both instances, by taking into account the forces to which the pin is subjected during mastication, a progressive weakening of the fastening of the pin to the maxilla bone very often occurs.

The present invention aims to eliminate the above described drawbacks of the prior art anchoring pins.

According to one feature of the invention, this aim is obtained by means of a self-threading pin comprising a drill or cutter shaped bit portion at one end, a substantially cylindrical, screw threaded shank portion and a driving head at the opposite end. By screwing the pin into a previously drilled bore in the maxilla bone, the drilling bit of the pin excavates a seat of a diameter corresponding to or otherwise fitting the cylindrical screw threaded shank of the pin, thus avoiding the danger of internal tensions as well as the danger of an unstable fastening of the pin. Or, stated differently, the drill bit has an effective cutting diameter substantially equal to the land areas of the intermediate shank portion of the pin. The thus obtained fastening is therefore optimal and this will result in a greater resistance of the pin to the stresses to which it is subjected during mastication, without progressively impairing the solidity of the fastening to the maxilla bone and thus assuring a longer duration of the dental prosthesis carried by the said pin.

BRIEF DESCRIPTION OF THE DRAWINGS

Further features and advantages of the self-threading pin according to the invention will be apparent from the following detailed description, taken with reference to the accompanying drawing, in which.

DESCRIPTION OF THE PREFERRED EMBODIMENT OF THE INVENTION

Figure 1:
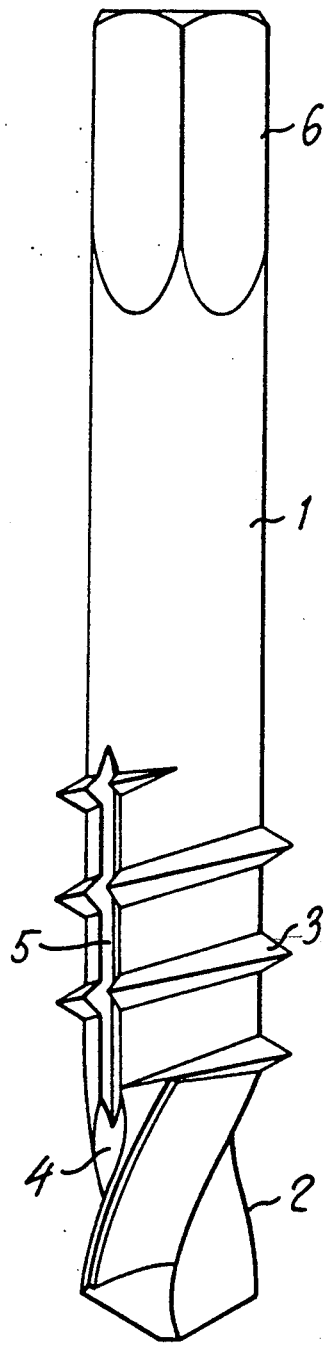
FIG. 1 is a side view of a pin for the implantation of a dental prosthesis according to a first embodiment of the invention.

With reference to the drawing, and with particular reference to FIG. 1, the self-threading pin for the implantation of a dental prosthesis shown herein comprises a cylindrical shank or body 1. At its lower end the cylindrical shank 1 is formed with a drill bit 2, particularly a twist drill bit. The intermediate portion of the shank 1 is provided with a screw thread 3. The threaded portion 3 of the shank 1 of the pin is further provided with longitudinal flutes 5, emerging from the discharge grooves 4 of the drill bit 2, and extending upwardly along the entire threaded portion of the shank 1 of the pin. The said flutes act as material discharge ducts, during the drilling operation. At its upper end the pin 1 is provided with a head 6 of suitable shape, for instance of square cross sectional shape, for its driving through a tool.

The operation of the described pin will be evident. At first, a bore of suitable dimensions is drilled into the maxilla bone. Thereafter, the pin according to the invention is driven into said bore. The drill bit 2 thereby excavates a seat, the diameter of which is exactly coincident with the diameter of the pin itself, while the following screw threaded portion only forms a seat for the screw threads in the walls of the bore drilled in the maxilla bone. In this manner the danger is eliminated that, due to a small boring deformation, stresses will be generated in the maxilla bone during the driving of the self-threading pin into said bone. On the other hand it is also obviated that, due to too large a bore drilled in the maxilla bone, an unstable fastening of the pin is provided, which would give rise to rocking movement of the pin during mastication. The discharge flutes 5 provide discharge of the material excavated by the drill bit out of the boring.

By the use of the pin according to the invention, a more stable and reliable fastening of a dental prosthesis to the maxilla bone is obtained, and the whole implantation operation is rendered more easy.

DESCRIPTION OF A FURTHER EMBODIMENT OF THE INVENTION

Figure 2:
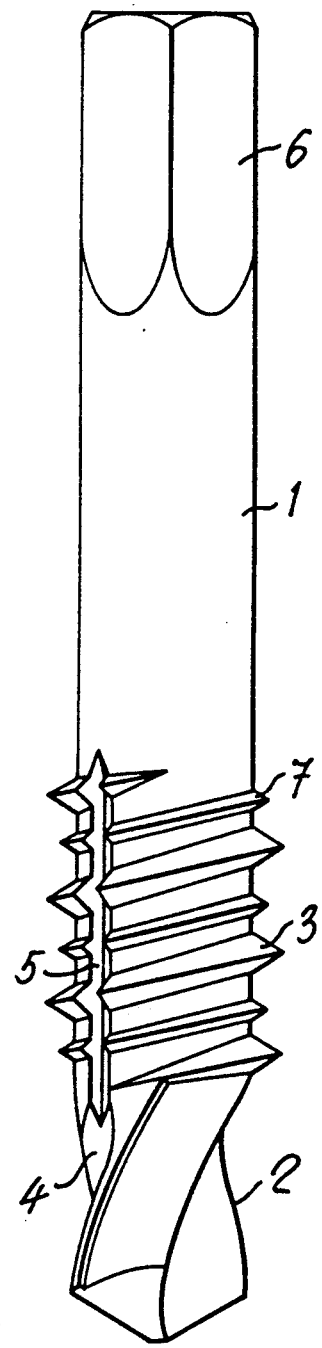
FIG. 2 is a side view of a pin according to a modified embodiment of the invention.

In FIG. 2 a further embodiment of the self-threading, self-drilling pin according to the invention 1 is shown. According to this embodiment, the screw threaded portion of the pin 1 is provided with two intercalated screw threads 3,7 of different heights. The screw thread 7 which is of lesser height provides a further abutment surface between the turns of the screw thread 3 of greater height, maintaining substantially invariated the pitch of the screw thread 3 and conferring a greater solidity to the fastening of the pin.

We claim:

1. A self-threading pin to be screw-threaded into the maxilla bone for the implantation of a dental prosthesis comprising an intermediate screw-threaded shank portion, a driving head at one end of the shank portion and a drill bit at the other end of said shank portion, said screw-threaded shank portion of the pin being provided with two intercalated screw threads of different heights.

2. A self-threading pin according to claim 1, in which the said screw-threaded shank portion has a substantially cylindrical profile.

3. A self-threading pin according to claim 1, in which the said drill bit is a helical drill bit.

4. A self-threading pin according to claim 1, further provided with at least one discharge flute, extending from the said drill bit along the said screw-threaded shank portion.

5. A self-threading pin according to claim 1, in which the said driving head is a polygonal driving head.

6. A self-threading anchoring pin structure to be permanently anchored into maxilla bone tissue for the implantation of a dental prosthesis, comprising:

a helical drill bit at the lower end of said pin, said drill bit constructed to drill out a previously formed bore hole in the bone, a driving head at the upper end of the pin, said driving head having means engagable for driving the drill bit into the bone tissue surrounding the previously formed bore hole, an intermediate screw-threaded shank portion including at least one helical thread and cylindrical land areas between the threads, the helical drill bit having an effective cutting diameter substantially equal to the diameter of said cylindrical land areas, so as to substantially match the cylindrical land areas with the inside surface of the bore hole drilled out by said drill bit, and at least one discharge flute extending from said drill bit along the screw-threaded shank portion for discharging material drilled by the drill bit.

7. A self-threading anchoring pin according to claim 6, wherein said screw-threaded shank portion of the pin is provided with two intercalated screw threads of different heights.

8. A self-threading anchoring pin according to claim 6, wherein the said driving head is a polygonal driving head.

* * * * *